US 7,514,091 B2

(12) United States Patent
Restle et al.

(10) Patent No.: US 7,514,091 B2
(45) Date of Patent: Apr. 7, 2009

(54) AMINATED SILICONE DETERGENT COSMETIC COMPOSITION AND USE

(75) Inventors: Serge Restle, Saint-Prix (FR); Claude Dubief, Le Chesnay (FR)

(73) Assignee: L'Oreal S.A., Paris (FR)

( * ) Notice: Subject to any disclaimer, the term of this patent is extended or adjusted under 35 U.S.C. 154(b) by 568 days.

(21) Appl. No.: 09/360,521

(22) Filed: Jul. 23, 1999

(65) Prior Publication Data

US 2002/0006389 A1 Jan. 17, 2002

(30) Foreign Application Priority Data

Jul. 23, 1998 (FR) .................................. 98 09414

(51) Int. Cl.
- A61K 8/02 (2006.01)
- A61K 8/00 (2006.01)
- A61K 31/695 (2006.01)
- A61Q 5/12 (2006.01)
- A61Q 5/00 (2006.01)
- C11D 1/62 (2006.01)

(52) U.S. Cl. .................... 424/401; 424/70.1; 424/70.12; 424/70.19; 424/70.21; 424/70.22; 424/70.28; 514/63; 514/881

(58) Field of Classification Search ................. 424/401, 424/70.1, 70.12, 70.19, 70.21, 70.22, 70.28, 424/70.11, 70.122, 7.15, 7.16; 514/881, 514/63
See application file for complete search history.

(56) References Cited

U.S. PATENT DOCUMENTS

| | | | |
|---|---|---|---|
| 2,528,378 A | | 10/1950 | Manheimer |
| 2,781,354 A | | 2/1957 | Manheimer |
| 4,185,087 A | | 1/1980 | Morlino |
| 5,198,209 A | * | 3/1993 | Zhou et al. ..................... 424/71 |
| 5,439,673 A | * | 8/1995 | Murray .................... 424/70.12 |
| 5,476,649 A | * | 12/1995 | Naito et al. ................. 424/70.1 |
| 5,567,428 A | * | 10/1996 | Hughes ....................... 424/401 |
| 5,578,298 A | | 11/1996 | Berthiaume et al. |
| 5,587,155 A | * | 12/1996 | Ochiai et al. ............. 424/70.28 |
| 5,650,383 A | | 7/1997 | Dubief et al. |
| 5,656,257 A | * | 8/1997 | Fealy et al. ............... 424/70.13 |
| 5,672,576 A | * | 9/1997 | Behrens et al. ............. 510/127 |
| 5,683,625 A | | 11/1997 | Berthiaume et al. |
| 5,883,058 A | * | 3/1999 | Wells et al. ................. 510/127 |
| 5,932,201 A | * | 8/1999 | de Labbey et al. ....... 424/70.17 |
| 5,935,561 A | * | 8/1999 | Inman et al. ............. 424/70.19 |
| 5,955,066 A | * | 9/1999 | Sako et al. ................ 424/70.12 |
| 5,977,036 A | * | 11/1999 | Guskey ....................... 510/121 |
| 6,001,376 A | * | 12/1999 | Mahieu et al. .............. 424/401 |
| 6,015,574 A | * | 1/2000 | Cannell et al. .............. 424/450 |
| 6,022,836 A | * | 2/2000 | Dubief et al. ............... 510/122 |
| 6,028,041 A | * | 2/2000 | Decoster et al. ............. 510/119 |
| 6,153,570 A | | 11/2000 | Decoster |
| 6,159,914 A | * | 12/2000 | DeCoster et al. ............ 510/119 |
| 6,162,423 A | * | 12/2000 | Sebag et al. .............. 424/70.12 |
| 6,162,424 A | * | 12/2000 | Decoster et al. .......... 424/70.17 |
| 6,165,455 A | * | 12/2000 | Torgerson et al. ........ 424/70.12 |
| 6,180,117 B1 | | 1/2001 | Berthiaume et al. |
| 6,194,363 B1 | * | 2/2001 | Murray ....................... 510/119 |
| 6,200,554 B1 | * | 3/2001 | Yeoh et al. ............... 424/70.12 |
| 6,210,691 B1 | * | 4/2001 | Mahieu et al. .............. 424/401 |
| 6,290,944 B1 | * | 9/2001 | Garnier et al. ........... 424/70.21 |
| 6,451,747 B1 | | 9/2002 | Decoster |
| 2001/0031270 A1 | * | 10/2001 | Douin et al. ................ 424/401 |

FOREIGN PATENT DOCUMENTS

| | | |
|---|---|---|
| DE | 195 18 449 A1 | 11/1995 |
| EP | 0 095 238 | 11/1983 |
| EP | 0 337 354 | 10/1989 |
| EP | 0 180 464 B1 | 1/1990 |
| EP | 0 275 707 B1 | 5/1992 |
| EP | 0 870 491 | 10/1998 |
| EP | 0 870 491 B1 | 2/2001 |
| EP | 0 811 371 B1 | 3/2003 |
| FR | 2 270 846 | 12/1975 |
| FR | 2 383 660 | 10/1978 |
| FR | 2 470 596 | 6/1981 |
| FR | 2 519 863 | 7/1983 |
| FR | 2 598 611 | 11/1987 |
| FR | 2 761 598 | 10/1998 |
| GB | 2 255 101 A | 10/1992 |
| JP | 4-327520 | 11/1992 |
| JP | 08-59994 | 3/1996 |
| JP | 8-217643 | 8/1996 |
| WO | WO 93/08787 | 5/1993 |
| WO | WO 94/06403 | 3/1994 |
| WO | WO 95/01152 | 1/1995 |
| WO | WO 96/32919 | 10/1996 |
| WO | WO 97/46211 | 12/1997 |

OTHER PUBLICATIONS

English Translation of WO 97/46211 published Dec. 11, 1997.*
English language Derwent Abstract of EP 0 870 491.
English language Derwent Abstract of FR 2 270 846.
English language Derwent Abstract of FR 2 383 660.
English language Derwent Abstract of FR 2 470 596.
English language Derwent Abstract of FR 2 519 863.
English language Derwent Abstract of FR 2 598 611.
English language Derwent Abstract of FR 2 761 598.

* cited by examiner

*Primary Examiner*—Shengjun Wang
(74) *Attorney, Agent, or Firm*—Finnegan, Henderson, Farabow, Garrett & Dunner, L.L.P.

(57) ABSTRACT

Detergent and conditioning compositions comprising, in a cosmetically acceptable medium, (A) a washing base comprising at least one anionic surfactant and at least one amphoteric surfactant and (B) at least one aminated silicone having an amine number greater than or equal to 0.4 meq/g, the amphoteric surfactant/anionic surfactant ratio by weight being greater than or equal to 0.2. The use of detergent and conditioning compositions for cleaning and for caring of the hair or the skin.

47 Claims, No Drawings

AMINATED SILICONE DETERGENT COSMETIC COMPOSITION AND USE

The present invention relates to novel cosmetic compositions with improved properties intended simultaneously for cleaning and for conditioning keratinous substances, such as the hair, and comprising, in a cosmetically acceptable aqueous vehicle, a washing base composed of anionic and amphoteric surfactants in which is also present an aminated silicone having an amine number greater than or equal to 0.4 meq/g. The invention also relates to the use of the said compositions in the abovementioned cosmetic application.

Detergent compositions (such as shampoos) based essentially on conventional surface-active agents of, in particular, anionic, non-ionic and/or amphoteric type, but more particularly of anionic type, are commonly used for cleaning and/or washing keratinous substances, such as the hair. These compositions are applied to wet hair and the foam generated by massaging or rubbing with the hands makes it possible, after rinsing with water, to remove the various types of dirt initially present on the hair or the skin.

These base compositions certainly have a good washing power but the intrinsic cosmetic properties which are attached to them remain fairly weak, however, in particular because of the fact that the relatively aggressive nature of such a cleaning treatment can, in the long term, result in more or less marked damage to the hair fiber, related in particular to the gradual removal of the lipids or proteins held in or at the surface of the hair fiber.

Consequently, to improve the cosmetic properties of the above detergent compositions, and more particularly of those which are called upon to be applied to sensitized hair (i.e. hair which is found to be damaged or embrittled, in particular under the chemical action of atmospheric agents and/or of hair treatments, such as permanent waves, dyeings or bleachings), it is now usual to introduce into the latter additional cosmetic agents, known as conditioning agents, intended mainly to repair or limit the harmful or undesirable effects induced by the various treatments or attacks to which the hair fibers are more or less repeatedly subjected. These conditioning agents can, of course, also improve the cosmetic behaviour of natural hair.

Provision has already been made to use silicones and more particularly insoluble silicones for this purpose. Insoluble compounds and more particularly silicones exhibit the disadvantage of being difficult to maintain as an even dispersion in the medium.

Provision has already been made, to maintain silicones in suspension, to use ester or ether derivatives comprising a long chain (pearlescent agents) or polysaccharides, such as xanthan gum (gelling agents). However, the pearlescent agents can exhibit problems of crystallization, which sometimes result in a change (increase) in the viscosity of the compositions over time; the gelling agents can also exhibit disadvantages, namely, on the one hand, that the foam of the detergent compositions comprising polysaccharides is difficult to develop (poor initiation of foam) and that, on the other hand, the compositions do not have a smooth texture and flow in waves, which is not very highly appreciated by the users. Furthermore, these various suspending agents may not make it possible to obtain transparent or clear compositions.

The aim of the present invention is to provide compositions which preferably do not exhibit any of the disadvantages of the above-mentioned compositions.

The silicones must also be carried on the treated keratinous substances with a view to conferring on them, depending on the application, properties of softness, of gloss and of disentangling, without leading to a greasy nature.

Thus, following considerable research carried out on the question, it has now been found by the inventors that, by using a specific washing base and at least one aminated silicone having an amine number greater than or equal to 0.4 meq/g and of the formulae (I) and (IV) set forth herein, it is possible to obtain stable and transparent detergent compositions exhibiting excellent cosmetic properties, in particular ease of styling, disentangling, and body of the treated hair, and having good properties during use, such as a good intrinsic washing power and a good foaming power.

The industrial implementation is extremely easy, and the cosmetic properties of the shampoos are excellent.

The compositions in accordance with the invention confer on the hair, after rinsing, a notable treating effect which is displayed in particular by an ease of disentangling and a contribution of body, lightness, sleekness, softness and suppleness, without any feeling of greasiness.

Thus, in one aspect, the present invention is novel detergent and conditioning cosmetic compositions, characterized in that they comprise, in a cosmetically acceptable aqueous medium, (A) a base comprising at least one anionic surfactant and at least one amphoteric surfactant and (B) a conditioner system comprising at least one aminated silicone chosen from those of formulae (I) and (IV) below, the amine number of which is greater than or equal to 0.4 meq/g, the amphoteric surfactant/anionic surfactant ratio by weight being greater than or equal to 0.2:1

Another aspect of the invention relates to the use in cosmetics of the above compositions for cleaning and/or removing make-up from and/or conditioning keratinous substances, such as the hair and the skin.

A—Washing Base;

The washing base comprises one or more anionic surfactants and one or more amphoteric surfactants.

(i) Anionic Surfactant(s):

Their nature does not assume a really critical character within the context of the present invention.

Thus, mention may in particular be made, by way of example of anionic surfactants which can be used, alone or as mixtures, in the context of the present invention, of (nonlimiting list) the salts (in particular alkali metal, especially sodium, salts, ammonium salts, amine salts, aminoalcohol salts or magnesium salts) of the following compounds: alkyl sulphates, alkyl ether sulphates, alkylamido ether sulphates, alkylaryl polyether sulphates or monoglyceride sulphates; alkyl sulphonates, alkyl phosphates, alkylamido sulphonates, alkylaryl sulphonates, α-olefin sulphonates or paraffin sulphonates; alkyl sulphosuccinates, alkyl ether sulphosuccinates or alkylamido sulphosuccinates; alkylsulphosuccinamates; alkyl sulphoacetates; alkyl ether phosphates; acylsarcosinates; acylisethionates and N-acyltaurates, the alkyl or acyl radical of all these different compounds preferably comprising from 12 to 20 carbon atoms and the aryl radical preferably denoting a phenyl or benzyl group. Mention may also be made, among the anionic surfactants which can be further used, of the salts of fatty acids, such as the salts of oleic, ricinoleic, palmitic and stearic acids, or the acids of coconut oil or of hydrogenated coconut oil; or acyllactylates in which the acyl radical comprises 8 to 20 carbon atoms. Use may also be made of weakly anionic surfactants, such as alkyl D-galactoside uronic acids and their salts, as well as of polyoxyalkylenated ($C_6$-$C_{24}$)alkyl ether carboxylic acids, polyoxyalkylenated ($C_6$-$C_{24}$) alkylaryl ether carboxylic acids, polyoxyalkylenated ($C_6$-$C_{24}$)alkylamido ether carboxylic acids and their salts, in particular those comprising from 2 to 50 ethylene oxide groups, and their mixtures.

Use is preferably made of an anionic surface-active agent chosen from sodium, triethanolamine and ammonium ($C_{12}$-$C_{14}$)alkyl sulphates, sodium ($C_{12}$-$C_{14}$)alkyl ether sulphates oxyethylenated with 2.2 mol of ethylene oxide, sodium cocoylisethionate, and sodium α-($C_{14}$-$C_{16}$)-olefin sulphonate.

Among the anionic surfactants, it is preferable to use, according to the invention, alkyl sulphate and alkyl ether sulphate salts and their mixtures.

(ii) Amphoteric Surfactant(s):

The amphoteric surface-active agents, the nature of which does not assume any critical character in the context of the present invention, may be in particular (nonlimiting list) derivatives of aliphatic secondary or tertiary amines in which the aliphatic radical is a linear or branched chain comprising 8 to 22 carbon atoms and comprising at least one water-solubilizing anionic group (for example carboxylate, sulphonate, sulphate, phosphate or phosphonate); mention may also be made of ($C_8$-$C_{20}$)alkyl betaines, sulphobetaines, ($C_8$-$C_{20}$) alkyl amido($C_1$-$C_6$)alkyl betaines or ($C_8$-$C_{20}$)alkyl amido ($C_1$-$C_6$)alkyl sulphobetaines.

Mention may be made, among the amine derivatives, of the products sold under the trade name MIRANOL®, as disclosed in U.S. Pat. No. 2,528,378 and U.S. Pat. No. 2,781,354, the disclosures of each of which are herein specifically incorporated by reference, and with structures:

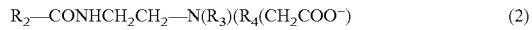

$$R_2\text{—CONHCH}_2\text{CH}_2\text{—N}(R_3)(R_4(CH_2COO^-)) \quad (2)$$

in which: $R_2$ is chosen from alkyl radicals derived from an acid $R_2$—COOH present in hydrolysed coconut oil, and or heptyl, nonyl and undecyl radicals; $R_3$ is chosen from β-hydroxyethyl groups; and, $R_4$ is chosen from carboxymethyl groups; and

$$R_{2'}\text{—CONHCH}_2\text{CH}_2\text{—N}(B)(C) \quad (3)$$

in which:

B is chosen from —$CH_2CH_2OX'$ groups; C is chosen from —$(CH_2)_z$—Y' groups, with z=1 or 2;

X' is chosen from the —$CH_2CH_2$—COOH group and a hydrogen atom;

Y' is chosen from —COOH and the —$CH_2$—CHOH—$SO_3H$ radical;

$R_{2'}$ is chosen from alkyl radicals of an acid $R_9$—COOH present in hydrolysed linseed oil or coconut oil, alkyl radicals, in particular a $C_7$, $C_9$, $C_{11}$ or $C_{13}$ radical, $C_{17}$ alkyl radicals and their iso form, and unsaturated $C_{17}$ radicals.

Such compounds are classified in the CTFA dictionary, 5th Edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid and Cocoamphodipropionic acid. Mention may be made, by way of example, of the cocoamphodiacetate sold under the trade name MIRANOL® C2M concentrate by the company Rhône-Poulenc.

According to the present invention, it is more particularly preferred to use the amphoteric surface-active agents belonging to the group of the betaines, such as the alkyl betaines, in particular the cocoyl betaine sold under the trade name "DEHYTON AB 30" as an aqueous solution comprising 30% of AM by the company Henkel, or the alkylamido betaines, such as those having the trade name TEGOBETAINE® F50, sold by the company Goldschmidt.

The minimum amount of washing base is an amount effective to confer a satisfactory foaming and/or detergent power on the final composition. Excessively large amounts of washing base do not really contribute additional advantages. Thus, according to the invention, the washing base can be present in the composition in an amount ranging from 4% to 50% by weight, preferably from 6% to 35% by weight, and more preferably still from 8% to 25% by weight, relative to the total weight of the final composition.

By way of example, the detergent compositions in accordance with the invention generally comprise:

(i) at least one anionic surfactant: from 3 to 30% by weight, preferably from 5 to 20% by weight, with respect to the total weight of the detergent composition;

(ii) at least one amphoteric surfactant: from 1 to 20% by weight, preferably from 1.5 to 15% by weight, with respect to the total weight of the detergent composition.

The amphoteric surfactant/anionic surfactant ratio by weight preferably ranges from 0.2:1 to 10:1, more particularly from 0.25:1 to 5:1, and more particularly still from 0.3:1 to 3:1.

B—Aminated Silicone

As explained, the compositions according to the invention comprise a water-insoluble aminated silicone, the amine number of which is greater than or equal to 0.4 meq/g, preferably from 0.5 to 5 meq/g and more particularly from 0.5 to 3.5 meq/g.

The amine number is the number of amine milliequivalents per gram of compound. This number can be determined by methods conventional in the art, for example by titration methods with a colored indicator or by potentiometric titration.

The term "water-insoluble" is understood as meaning that a solution at a concentration of 1% by weight in water is not substantially transparent to the naked eye at 25° C.

According to the invention, aminated silicone denotes any silicone comprising at least one primary, secondary or tertiary amine or one quaternary ammonium group, as follows:

(a) aminated silicone polymers corresponding to the formula:

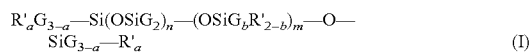

$$R'_a G_{3-a}\text{—Si}(OSiG_2)_n\text{—}(OSiG_bR'_{2-b})_m\text{—O—SiG}_{3-a}\text{—R'}_a \quad (I)$$

in which:

G is chosen from a hydrogen atom, phenyl, OH and $C_1$-$C_8$ alkyl groups, for example a methyl group;

a is chosen from the number 0 and an integer from 1 to 3, preferably 0;

b is chosen from 0 and 1, preferably 1;

m and n are numbers such that the sum (n+m) can vary, preferably varying from 1 to 2000, more preferably varying from 50 to 150, wherein n is chosen from a number from 0 to 1999, preferably from 49 to 149 and wherein m can be chosen from a number from 1 to 2000, preferably from 1 to 10;

R' is chosen from monovalent radicals of formula —$C_qH_{2q}L$, in which q is chosen from a number from 2 to 8 and L is chosen from optionally quaternized amino groups chosen from:

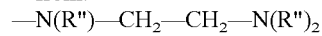
—N(R")—$CH_2$—$CH_2$—N(R")$_2$

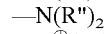
—N(R")$_2$

—$N^\oplus$(R")$_3$A$^-$

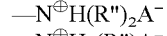
—$N^\oplus$H(R")$_2$A$^-$

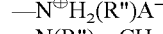
—$N^\oplus$H$_2$(R")A$^-$

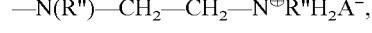
—N(R")—$CH_2$—$CH_2$—$N^\oplus$R"H$_2$A$^-$, in which: R", which can be identical or different, can be chosen from a hydrogen atom, and phenyl, benzyl and saturated monovalent hydrocarbon-comprising radicals, for example, an alkyl radical having from 1 to 20 carbon atoms, preferably a methyl radical, and $A^-$ is chosen from organic and inorganic anions, for example a halide ion, such as, for example, fluoride, chloride, bromide or iodide.

Products corresponding to the definition of group (a) silicone polymers are in particular:

the polymer named "trimethylsilylamodimethicone" (International Cosmetic Ingredient Dictionary and Handbook, Seventh Edition, 1997), corresponding to the formula:

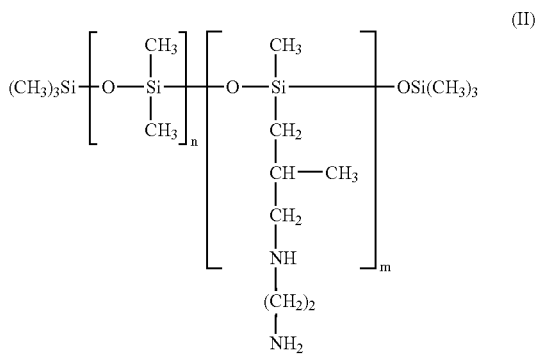

(II)

in which n and m have the meanings given above (cf. formula (I)), the polymer named "amodimethicone" (International Cosmetic Ingredient Dictionary and Handbook, Seventh Edition, 1997), corresponding to the formula:

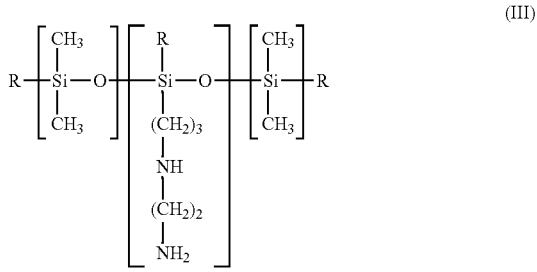

(III)

in which R is chosen from OH and methyl.

Such polymers are disclosed, for example, in Patent Application EP-A-95,238, the disclosure of which is herein incorporated by reference.

(b) cationic silicone polymers corresponding to the following formula(IV):

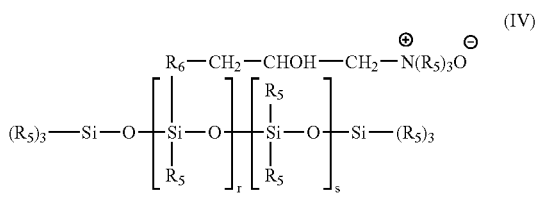

(IV)

in which:

$R_5$ can be the same or different and is chosen from monovalent hydrocarbon-comprising radicals having from 1 to 18 carbon atoms, preferably $C_1$-$C_{18}$ alkyl and $C_2$-$C_{18}$ alkenyl radicals, for example a methyl radical;

$R_6$ is chosen from divalent hydrocarbon-comprising radicals, preferably $C_1$-$C_{18}$ alkylene radicals and divalent $C_1$-$C_{18}$ alkyleneoxy radicals, for example a $C_1$-$C_8$ radical;

$Q^-$ is chosen from organic or inorganic anions, for example a halide ion, in particular a chloride ion;

r represents a mean statistical value of 2 to 20, preferably 2 to 8;

s represents a mean statistical value of 20 to 200, preferably 20 to 50.

Such polymers are disclosed more particularly in U.S. Pat. No. 4,185,087, the disclosure of which is herein incorporated by reference.

Aminated silicones which are particularly well suited according to the invention are the trimethylsilylamodimethicones sold by the company Wacker under the trade name FINISH WT 1650 or by the company General Electric under the trade name SF 1708 or the amodimethicones sold by the company Wacker under the trade names FINISH WT 1600 and L 650 or by the company Genese under the trade name SP4 SILICONE FLUID.

The silicone or silicones can be used in the compositions in accordance with the invention in concentrations generally from 0.05 to 15% and preferably from 0.2 to 10% by weight with respect to the total weight of the composition and more particularly still from 0.5 to 5% by weight.

The cosmetically acceptable aqueous medium can be composed solely of water or of a mixture of water and of a cosmetically acceptable solvent, such as a lower $C_1$-$C_{12}$ alcohol, for example ethanol, isopropanol, tert-butanol, n-butanol, hexanol or decanol; polyols, such as alkylene glycols, for example propylene glycol, glycerol and poly(alkylene glycol)s; or glycol ethers.

The solvent or solvents can be used in concentrations generally ranging from 0.1 to 20% by weight and more particularly from 0.2 to 10% by weight, relative to the weight of the composition.

The detergent compositions according to the invention preferably exhibit a final pH ranging from 3 to 8, more preferably from 4 to 6.5. The pH can be conventionally adjusted to the desired value by addition of a base (organic or inorganic) to the composition, for example sodium hydroxide, aqueous ammonia or a primary, secondary or tertiary (poly) amine, such as monoethanolamine, diethanolamine, triethanolamine, isopropanolamine or 1,3-propanediamine, or alternatively by addition of an inorganic or organic acid, preferably citric acid or hydrochloric acid.

The compositions in accordance with the invention can comprise, in addition to the combination defined above, viscosity regulating agents, such as electrolytes, or thickening agents. Mention may in particular be made of sodium chloride, sodium xylenesulphonate, scleroglucans, xanthan gums, fatty acid alkanolamides, alkyl ether carboxylic acid alkanolamides optionally oxyethylenated with up to 5 mol of ethylene oxide, such as the product sold under the trade name "AMINOL A15" by the company Chem Y, crosslinked poly (acrylic acid)s and crosslinked acrylic acid/$C_{10}$-$C_{30}$ alkyl acrylate copolymers. These viscosity regulating agents are used in the compositions according to the invention in proportions which can range up to 10% by weight with respect to the total weight of the composition.

The compositions in accordance with the invention can also comprise up to 5% of pearlescent or opacifying agents well known in the state of the art, such as, for example, fatty alcohols, sodium or magnesium palmitates, sodium or magnesium stearates and hydroxystearates, acylated derivatives comprising a fatty chain, such as ethylene glycol or polyethylene glycol monostearates or distearates, or ethers comprising fatty chains, such as, for example, distearyl ether or 1-(hexadecyloxy)-2-octadecanol.

The compositions in accordance with the invention can in addition optionally comprise other agents having the effect of improving the cosmetic properties of hair or of the skin without, however, detrimentally affecting the stability of the compositions. Mention may be made, in this respect, of cationic surface-active agents, anionic or non-ionic or cationic or amphoteric polymers, proteins, protein hydrolysates, ceramides, pseudoceramides, fatty acids comprising linear or branched $C_{16}$-$C_{40}$ chains, such as 18-methyleicosanoic acid, hydroxy acids, vitamins, panthenol, volatile or non-volatile silicones, other than the silicones of the invention, which are soluble or insoluble in the medium, UV screening agents, moisturizing agents, antidandruff or antiseborrhoeic agents, agents for combating free radicals, and their mixtures.

The cationic polymers which can be used in accordance with the present invention can be chosen from all those already known per se as improving the cosmetic properties of hair treated with detergent compositions, namely, in particular, those disclosed in Patent Application EP-A-0,337,354 and in French Patent Applications FR-A-2,270,846, 2,383,660, 2,598,611, 2,470,596 and 2,519,863, the disclosures of each are hereby incorporated by reference.

In a still more general way, within the meaning of the present invention, the expression "cationic polymer" denotes any polymer comprising cationic groups and/or groups which can be ionized to cationic groups.

Among all the cationic polymers capable of being used in the context of the present invention, preference is given to the employment of quaternary derivatives of cellulose ether, such as the products sold under the trade name "JR 400" by the company Union Carbide Corporation, cyclopolymers, in particular diallyldimethylammonium salt homopolymers and copolymers of diallyldimethylammonium salt and of acrylamide, in particular the chlorides, sold under the trade names "MERQUAT 100", "MERQUAT 550" and "MERQUAT S" by the company Merck, cationic polysaccharides and more particularly guar gums modified by 2,3-epoxypropyltrimethylammonium chloride, sold, for example, under the trade name "JAGUAR C13S" by the company Meyhall, optionally crosslinked homopolymers and copolymers of (meth)acryloyloxyethyltrimethylammonium salt, sold by the company Allied Colloids as a 50% solution in mineral oil under the trade names SALCARE SC92 (crosslinked copolymer of methacryloyloxyethyltrimethylammonium chloride and of acrylamide) and SALCARE SC95 (crosslinked homopolymer of methacryloyloxyethyltrimethylammonium chloride), or copolymers of vinylpyrrolidone and of methylvinylimidazolium salt, such as the products sold by BASF under the trade names LUVIQUAT FC 370, LUVIQUAT FC 550, LUVIQUAT FC 905 and LUVIQUAT HM-552.

Use may also be made of polymers which are composed of repeat units corresponding to the formula:

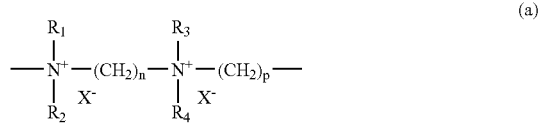

(a)

in which: $R_1$, $R_2$, $R_3$ and $R_4$, which are identical or different, are chosen from alkyl and hydroxyalkyl radicals having from 1 to 4 carbon atoms approximately; n and p are chosen from integers varying from 2 to 20 approximately and $X^-$ is chosen from anions derived from inorganic or organic acids.

A particularly preferred compound of formula (a) is that in which $R_1$, $R_2$, $R_3$ and $R_4$ represent a methyl radical and n=3, p=6 and X=Cl, known as Hexadimethrine chloride according to the INCI (CTFA) nomenclature.

According to the invention, the cationic polymer or polymers can be present in the composition in an amount ranging from 0.001% to 10% by weight, preferably from 0.005% to 5% by weight, and more preferably still from 0.01% to 3% by weight, relative to the total weight of the final composition.

The compositions according to the invention can also comprise foam synergists, such as $C_{10}$-$C_{18}$ 1,2-alkanediols or fatty alkanolamides derived from mono- or from diethanolamine.

Of course, a person skilled in the art will take care to choose this or these optional additional compounds and/or their amounts so that the advantageous properties intrinsically attached to the combination in accordance with the invention are not, or not substantially, detrimentally affected by the envisaged addition or additions.

The foaming power of the compositions according to the invention, characterized by a foam height, is generally greater than 75 mm, preferably greater than 100 mm, measured according to the modified Ross-Miles method (NF T 73-404/ISO696). The modifications to the method are as follows:

The measurement is carried out at a temperature of 22° C. with osmosed water. The concentration of the solution is 2 g/l. The height of the drop is 1 m. The amount of composition which drops is 200 ml. These 200 ml of composition fall in a measuring cylinder with a diameter of 50 mm containing 50 ml of the composition to be tested. The measurement is carried out 5 minutes after the composition has finished being run in.

The compositions can be provided in the form of more or less thickened liquids, of creams or of gels and they are preferably for washing or caring for keratinous substances, in particular the hair and the skin and more particularly still the hair.

The aminated silicone is generally added to the preheated composition comprising the surfactants and the water-soluble compounds.

Another subject matter of the invention is a process for washing and for conditioning keratinous substances, such as, in particular, the hair, which comprises applying, to the wetted said substances, an effective amount of a composition as defined above and in then rinsing with water, after an optional period of rest.

The compositions according to the invention are preferably used as shampoos for washing and conditioning the hair and they are applied, in that case, to wet hair in amounts which are effective for washing it and the foam generated by massaging or rubbing with the hands is subsequently removed, after an optional period of rest, by rinsing with water, it being possible for the operation to be repeated one or more times.

The compositions in accordance with the invention can also be used as shower gels for washing and conditioning the hair and/or the skin, in which case they are applied to the wet skin and/or hair and are rinsed after application.

Concrete but in no way limiting examples illustrating the invention will now be given.

EXAMPLE 1

Influence of the Amphoteric S/anionic S Ratio

Two shampoo compositions were prepared, one in accordance with the invention (composition A) and the other comparative (composition B):

|  | B Comparative | A Invention |
| --- | --- | --- |
| Sodium lauryl ether sulphate (70/30 $C_{12}$/$C_{14}$), comprising 2.2 mol of ethylene oxide, as an aqueous solution comprising 70% of AM (AM = active material) | 16.8 g AM | 15 AM |
| Cocoyl betaine (trade name DEHYTON AB 30) | 2.4 g AM | 5 g AM |
| Trimethylsilylamodimethicone, amine number 0.6 meq/g (trade name FINISH WT 1650 from Wacker) | 3 g | 3 g |
| Diallyldimethylammonium chloride homopolymer as an aqueous solution comprising 40% of AM (trade name MERQUAT 100 from Calgon) | 0.4 g AM | 0.4 g AM |
| NaCl | 3.25 g | 3.25 g |
| Fragrance, preservative | q.s. | q.s. |
| Hydrochloric acid, q.s. pH | 6 | 6 |
| Demineralized water, q.s. for | 100 g | 100 g |

The composition A according to the invention (amphoteric S/anionic S=0.33) is transparent.

The comparative composition B (amphoteric S/anionic S=0.14) is not transparent.

The transparency is evaluated by turbidimetry with a value of less than 25 NTU (Nephelometric turbidity units).

Shampooing was carried out by applying approximately 1 g of the composition A to locks of pre-wetted sensitized hair (2.5 g). The shampoo is induced to foam, is left standing for 10 min and is then copiously rinsed with water. The locks are towel dried.

The same procedure as above is carried out with the comparative composition B.

A panel of experts evaluated the appearance of the hair.

All the experts indicate that the hair treated with the composition A according to the invention disentangles more readily and is softer and smoother than the hair treated with the composition B.

EXAMPLE 2

Influence of the Amine Number

Shampoo compositions were produced with the following composition:

|  | A |
| --- | --- |
| Sodium lauryl ether sulphate (70/30 $C_{12}$/$C_{14}$), comprising 2.2 mol of ethylene oxide, as an aqueous solution comprising 70% of AM (AM = active material) | 15 g AM |
| Cocoyl betaine (trade name DEHYTON AB 30) | 5 g AM |
| Aminated silicone | 3 g |
| Diallyldimethylammonium chloride homopolymer as an aqueous solution comprising 40% of AM (trade name MERQUAT 100 from Calgon) | 0.4 g AM |
| NaCl | 3.25 g |
| Fragrance, preservative | q.s. |
| Hydrochloric acid, q.s. pH | 6 |
| Demineralized water q.s. for | 100 g |

The silicones tested were the following and the results are collated in the following table:

|  | AMINATED SILICONE |  | Amine number (meq/g) | Transparency |
| --- | --- | --- | --- | --- |
| 1 | Trimethylsilyl-amodimethicone | Trade name VP 1480 M (Wacker) | 0.12-0.15 | NO |
| 2 | Trimethylsilyl-amodimethicone | Trade name SILICONE FLUID F801 (Wacker) | 0.14 | NO |
| 3 | Amodimethicone | Trade name FINISH WR 100 (Wacker) | 0.15 | NO |
| 4 | Amodimethicone | Trade name FINISH WR 1300 (Wacker) | 0.3 | NO |
| 5 | Amodimethicone as an emulsion | Trade name SILSOFT TP 515 (OSI) | 0.058 | NO |
| 6 | Amodimethicone as an emulsion | Trade name DC939 (Dow Corning) | <0.1 | NO |
| 7 | Trimethylsilyl-amodimethicone | Trade name FINISH WT 1650 (Wacker) | 0.6 | YES |
| 8 | Trimethylsilyl-amodimethicone | Trade name SF 1708 (General Electric) | 0.8 | YES |
| 9 | Amodimethicone | Trade name FINISH WT 1600 (Wacker) | 0.6 | YES |
| 10 | Amodimethicone | Trade name SP4 SILICONE FLUID (Genese) | 0.75 | YES |
| 11 | Amodimethicone | Trade name L650 (Wacker) | 2.7-3.2 | YES |

The compositions 7 to 11 according to the invention are transparent, whereas the compositions (1 to 6) comprising a silicone with an amine number of less than 0.4 meq/g are not transparent.

The compositions 1 to 6 are stable, whereas the compositions 7 to 11 are not stable (the silicone is released at the surface of the composition).

What is claimed is:

1. A detergent and conditioning cosmetic composition, comprising:
   (A) a washing base comprising at least one anionic surfactant and at least one amphoteric surfactant, wherein the amphoteric surfactant/anionic surfactant ratio by weight is greater than or equal to 0.2:1;
   (B) a conditioner system comprising at least one aminated silicone having an amine number greater than or equal to 0.4 meq/g, said at least one aminated silicone being chosen from:
(a) aminated silicone polymers corresponding to the formula:

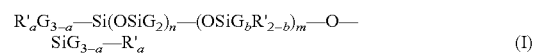

in which:
   G is chosen from a hydrogen atom, phenyl, OH, and $C_1$-$C_8$ alkyl groups;
   a is chosen from 0, 1, 2, and 3;
   b is chosen from 0 and 1;
   m and n are chosen from numbers such that the sum (n+m) varies from 1 to 2000;
   R' is chosen from monovalent radicals of formula —$C_qH_{2q}$L, wherein q is chosen from a number ranging from 2 to 8 and L is chosen from optionally quaternized amino groups chosen from:
   —N(R")—$CH_2$—$CH_2$—N(R")$_2$,
   —N(R")$_2$,
   —$N^p$(R")$_3$$A^-$,
   —$N^p$H(R")$_2$$A^-$,
   —$N^p$H$_2$(R")$A^-$, and
   —N(R")—$CH_2$—$CH_2$—$N^p$R"H$_2$$A^-$, wherein R″, which are identical or different, are chosen from a hydrogen atom, and phenyl, benzyl and saturated monovalent hydrocarbon-comprising radicals, and A⁻ is chosen from organic and inorganic anions; and
(b) cationic silicone polymers corresponding to the following formula (IV):

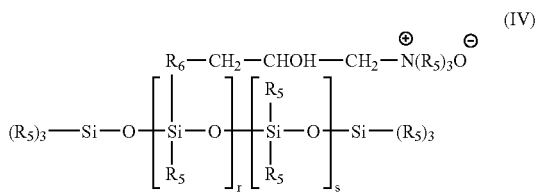

in which:
R₅ is chosen from monovalent hydrocarbon-comprising radicals having from 1 to 18 carbon atoms;
R₆ is chosen from divalent hydrocarbon-comprising radicals;
Q⁻ is chosen from organic and inorganic anions;
r represents a mean statistical value ranging from 2 to 20;
s represents a mean statistical value ranging from 20 to 200; and
(C) at least one cationic polymer;
wherein the composition is transparent.

2. The composition according to claim 1, wherein the amine number ranges from 0.5 to 5 meq/g.

3. The composition according to claim 1, wherein said washing base is present in said composition in an amount ranging from 4% to 50% by weight with respect to the total weight of the composition.

4. The composition according to claim 3, wherein the amount of washing base ranges from 6% to 35% by weight relative to the total weight of the composition.

5. The composition according to claim 4, wherein the amount of washing base ranges from 8% to 25% by weight relative to the total weight of the composition.

6. The composition according to claim 1, wherein said at least one anionic surfactant is present in said composition in an amount ranging from 3 to 30% by weight relative to the total weight of the composition.

7. The composition according to claim 6, wherein the amount of said at least one anionic surfactant ranges from 5% to 20% by weight relative to the total weight of the composition.

8. The composition according to claim 1, wherein the at least one amphoteric surfactant is present in said composition an amount ranging from 1 to 20% by weight, relative to the total weight of the composition.

9. The composition according to claim 8, wherein the amount of the at least one amphoteric surfactant ranges from 1.5 to 15% by weight, relative to the total weight of the composition.

10. The composition according to claim 1, wherein the amphoteric surfactant/anionic surfactant ratio by weight ranges from 0.2:1 to 10:1.

11. The composition according to claim 10, wherein the amphoteric surfactant/anionic surfactant ratio by weight ranges from 0.25:1 to 5:1.

12. The composition according to claim 11, wherein the amphoteric surfactant/anionic surfactant ratio by weight ranges from 0.3:1 to 3:1.

13. The composition according to claim 1, wherein G is a methyl group.

14. The composition according to claim 1, wherein a is 0.

15. The composition according to claim 1, wherein b is 1.

16. The composition according to claim 1, wherein the sum (n+m) varies from 50 to 150.

17. The composition according to claim 1, wherein n is chosen from the numbers 0 to 1999 and m is chosen from the numbers 1 to 2000.

18. The composition according to claim 17, wherein n is chosen from the numbers 49 to 149.

19. The composition according to claim 17, wherein m is chosen from the numbers 1 to 10.

20. The composition according to claim 1, wherein the saturated monovalent hydrocarbon-comprising radicals are chosen from alkyl radicals having from 1 to 20 carbon atoms.

21. The composition according to claim 20, wherein the saturated monovalent hydrocarbon-comprising radicals are a methyl radical.

22. The composition according to claim 1, wherein R₅ is chosen from C₁-C₁₈ alkyl and C₂-C₁₈ alkenyl radicals.

23. The composition according to claim 22, wherein R₅ is a methyl radical.

24. The composition according to claim 1, wherein R₆ is chosen from divalent C₁-C₁₈ alkylene radicals and divalent C₁-C₁₈ alkyleneoxy radicals.

25. The composition according to claim 24, wherein R₆ is chosen from divalent C₁-C₈ alkylene radicals and divalent C₁-C₈ alkyleneoxy radicals.

26. The composition according to claim 1, wherein the at least one aminated silicone is chosen from:
trimethylsilylamodimethicone polymers having the formula:

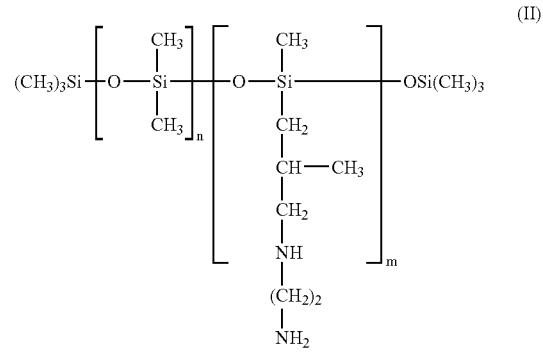

in which m and n are chosen from numbers such that the sum (n+m) ranges from 1 to 2000; and,
amodimethicone polymer having the formula:

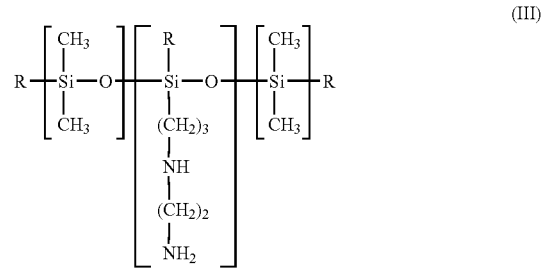

in which R is chosen from OH and methyl.

27. The composition according to claim 26, wherein n is chosen from the numbers 0 to 1999 and m is chosen from the numbers 1 to 2000.

28. The composition according to claim 27, wherein n is chosen from the numbers 49 to 149.

29. The composition according to claim 27, wherein m is chosen from the numbers 1 to 10.

30. The composition according to claim 1, wherein the at least one aminated silicone is present in said composition in an amount ranging from 0.05 to 15% by weight relative to the total weight of the composition.

31. The composition according to claim 30, wherein the amount of said at least one aminated silicone ranges from 0.2 to 10% by weight relative to the total weight of the composition.

32. The composition according to claim 1, wherein said composition further comprises at least one adjuvant chosen from cationic surface-active agents; anionic, non-ionic and amphoteric polymers; proteins; protein hydrolysates; ceramides; pseudoceramides; fatty acids comprising linear $C_{16}$-$C_{40}$ chains; fatty acids comprising branched $C_{16}$-$C_{40}$ chains; hydroxy acids; vitamins; panthenol; volatile and non-volatile silicones other than the silicones defined in formula (I) and (IV) of claim 1, said other silicones being soluble or insoluble in the medium; UV screening agents; moisturizing agents; antidandruff and antiseborrhoeic agents; and agents for combating free radicals.

33. The composition according to claim 32, wherein said fatty acid is 18-methyl-eicosanoic acid.

34. The composition according to claim 1, wherein the at least one cationic polymer is chosen from quaternary derivatives of cellulose ether; diallyldimethylammonium salt homopolymers; copolymers of diallyldimethylammonium salt and acrylamide; cationic polysaccharides; and copolymers of vinylpyrrolidone and methylvinylimidazolium salt.

35. The composition according to claim 1, wherein the at least one cationic polymer is chosen from polymers comprising repeat units corresponding to the formula:

$$-\underset{\underset{R_2}{|}}{\overset{\overset{R_1}{|}}{N^+}}-(CH_2)_n-\underset{\underset{R_4}{|}}{\overset{\overset{R_3}{|}}{N^+}}-(CH_2)_p- \quad\quad X^- \quad X^- \tag{a}$$

in which $R_1$, $R_2$, $R_3$ and $R_4$, which are identical or different, are chosen from alkyl and hydroxyalkyl radicals having from 1 to 4 carbon atoms, n and p are chosen from integers ranging from 2 to 20 and $X^-$ is chosen from anions of inorganic and organic acids.

36. The composition according to claim 1, wherein the at least one cationic polymer is present in said composition in an amount ranging from 0.001% to 10% by weight, relative to the total weight of the composition.

37. The composition according to claim 36, wherein the amount of the at least one cationic polymer ranges from 0.005% to 5% by weight, relative to the total weight of the composition.

38. The composition according to claim 37, wherein the amount of the at least one cationic polymer ranges from 0.01% to 3% by weight, relative to the total weight of the composition.

39. The composition according to claim 1, further comprising a cosmetically acceptable aqueous medium, wherein said medium is chosen from water and a mixture of water and a cosmetically acceptable solvent.

40. The composition according to claim 39, wherein the cosmetically acceptable solvent is chosen from $C_1$-$C_{12}$ alcohols, polyols, and glycol ethers.

41. The composition according to claim 40, wherein:
the $C_1$-$C_{12}$ alcohols are chosen from ethanol, isopropanol, tert-butanol, n-butanol, hexanol and decanol; and
the polyols are chosen from alkylene glycols.

42. The composition according to claim 41 wherein the alkylene glycols are chosen from propylene glycol, glycerol and poly(alkylene glycol)s.

43. The composition according to claim 39, wherein said solvent is present in an amount ranging from 0.1 to 20% by weight relative to the total weight of the composition.

44. A composition for cleaning or removing make-up from keratinous substances, or for conditioning keratinous substances, comprising:
(A) a washing base comprising at least one anionic surfactant and at least one amphoteric surfactant, wherein the amphoteric surfactant/anionic surfactant ratio by weight is greater than or equal to 0.2:1;
(B) a conditioner system comprising at least one aminated silicone having an amine number greater than or equal to 0.4 meq/g, said at least one aminated silicone being chosen from:
(a) aminated silicone polymers corresponding to the formula:

$$R'_a G_{3-a}-Si(OSiG_2)_n-(OSiG_b R'_{2-b})_m-O-SiG_{3-a}-R'_a \tag{I}$$

in which:
G is chosen from a hydrogen atom, phenyl, OH, and $C_1$-$C_8$ alkyl groups;
a is chosen from 0, 1, 2, and 3;
b is chosen from 0 and 1;
m and n are chosen from numbers such that the sum (n+m) varies from 1 to 2000;
R' is chosen from monovalent radicals of formula $-C_q H_{2q} L$, wherein q is chosen from a number ranging from 2 to 8 and L is chosen from optionally quaternized amino groups chosen from:
—N(R")—$CH_2$—$CH_2$—N(R")$_2$,
—N(R")$_2$,
—N$^p$(R")$_3$A$^-$,
—N$^p$H(R")$_2$A$^-$,
—N$^p$H$_2$(R")A$^-$, and
—N(R")—$CH_2$—$CH_2$—N$^p$R"H$_2$A$^-$,
wherein R", which are identical or different, are chosen from a hydrogen atom, and phenyl, benzyl and saturated monovalent hydrocarbon-comprising radicals, and A$^-$ is chosen from organic and inorganic anions; and
(b) cationic silicone polymers corresponding to the following formula (IV):

$$(R_5)_3-Si-O-\left[\underset{\underset{R_5}{|}}{\overset{\overset{R_5}{|}}{Si}}-O\right]_r \left[\underset{\underset{R_5}{|}}{\overset{\overset{R_6-CH_2-CHOH-CH_2-\overset{\oplus}{N}(R_5)_3 \overset{\ominus}{O}}{|}}{Si}}-O\right]_s -Si-(R_5)_3 \tag{IV}$$

in which:
$R_5$ is chosen from monovalent hydrocarbon-comprising radicals having from 1 to 18 carbon atoms;

$R_6$ is chosen from divalent hydrocarbon-comprising radicals;

$Q^-$ is chosen from organic and inorganic anions;

r represents a mean statistical value ranging from 2 to 20;

s represents a mean statistical value ranging from 20 to 200; and (C) at least one cationic polymer;

wherein the composition is transparent.

45. A shampoo comprising:

(A) a washing base comprising at least one anionic surfactant and at least one amphoteric surfactant, wherein the amphoteric surfactant/anionic surfactant ratio by weight is greater than or equal to 0.2:1;

(B) a conditioner system comprising at least one aminated silicone having an amine number greater than or equal to 0.4 meq/g, said at least one aminated silicone being chosen from:

(a) aminated silicone polymers corresponding to the formula:

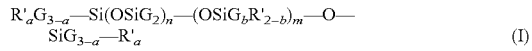
(I)

in which:

G is chosen from a hydrogen atom, phenyl, OH, and $C_1$-$C_8$ alkyl groups;

a is chosen from 0, 1, 2, and 3;

b is chosen from 0 and 1;

m and n are chosen from numbers such that the sum (n+m) varies from 1 to 2000;

R' is chosen from monovalent radicals of formula —$C_qH_{2q}L$, wherein q is chosen from a number ranging from 2 to 8 and L is chosen from optionally quaternized amino groups chosen from:

—N(R")—$CH_2$—$CH_2$—N(R")$_2$,

—N(R")$_2$,

—$N^p$(R")$_3A^-$,

—$N^pH$(R")$_2A^-$,

—$N^pH_2$(R")$A^-$, and

—N(R")—$CH_2$—$CH_2$—$N^pR"H_2A^-$, wherein R", which are identical or different, are chosen from a hydrogen atom, and phenyl, benzyl and saturated monovalent hydrocarbon-comprising radicals, and $A^-$ is chosen from organic and inorganic anions; and (b) cationic silicone polymers corresponding to the following formula (IV):

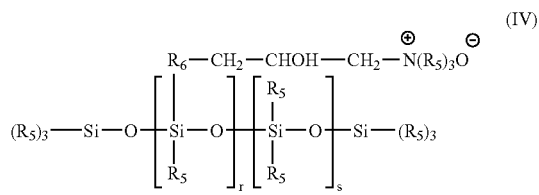
(IV)

in which:

$R_5$ is chosen from monovalent hydrocarbon-comprising radicals having from 1 to 18 carbon atoms;

$R_6$ is chosen from divalent hydrocarbon-comprising radicals;

$Q^-$ is chosen from organic and inorganic anions;

r represents a mean statistical value ranging from 2 to 20;

s represents a mean statistical value ranging from 20 to 200; and (C) at least one cationic polymer;

wherein the composition is transparent.

46. A process for washing and for conditioning keratinous substances, comprising:

applying an effective amount of a detergent and conditioning cosmetic composition to wetted keratinous substances; and, subsequently, rinsing said keratinous substances with water, after an optional period of rest, said detergent and conditioning cosmetic composition comprising:

(A) a washing base comprising at least one anionic surfactant and at least one amphoteric surfactant, wherein the amphoteric surfactant/anionic surfactant ratio by weight is greater than or equal to 0.2:1;

(B) a conditioner system comprising at least one aminated silicone having an amine number greater than or equal to 0.4 meq/g, said at least one aminated silicone being chosen from:

(a) aminated silicone polymers corresponding to the formula:

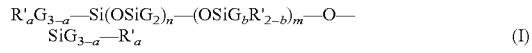
(I)

in which:

G is chosen from a hydrogen atom, phenyl, OH, and $C_1$-$C_8$ alkyl groups;

a is chosen from 0, 1, 2, and 3;

b is chosen from 0 and 1;

m and n are chosen from numbers such that the sum (n+m) varies from 1 to 2000;

R' is chosen from monovalent radicals of formula —$C_qH_{2q}L$, wherein q is chosen from a number ranging from 2 to 8 and L is chosen from optionally quaternized amino groups chosen from:

—N(R")—$CH_2$—$CH_2$—N(R")$_2$,

—N(R")$_2$,

—$N^p$(R")$_3A^-$,

—$N^pH$(R")$_2A^-$,

—$N^pH_2$(R")$A^-$, and

—N(R")—$CH_2$—$CH_2$—$N^pR"H_2A^-$, wherein R", which are identical or different, are chosen from a hydrogen atom, and phenyl, benzyl and saturated monovalent hydrocarbon-comprising radicals, and $A^-$ is chosen from organic and inorganic anions; and (b) cationic silicone polymers corresponding to the following formula (IV):

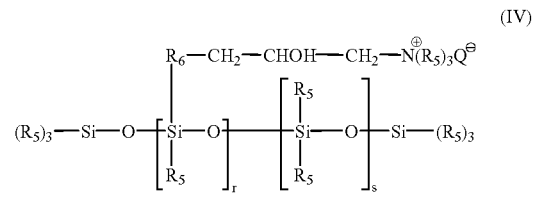
(IV)

in which:

$R_5$ is chosen from monovalent hydrocarbon-comprising radicals having from 1 to 18 carbon atoms;

$R_6$ is chosen from divalent hydrocarbon-comprising radicals;

$Q^-$ is chosen from organic and inorganic anions;

r represents a mean statistical value ranging from 2 to 20;

s represents a mean statistical value ranging from 20 to 200; and (C) at least one cationic polymer;

wherein the composition is transparent.

47. A detergent and conditioning cosmetic composition, comprising:

(A) a washing base comprising at least one anionic surfactant and at least one amphoteric surfactant, wherein the amphoteric surfactant/anionic surfactant ratio by weight ranges from 0.2:1 to 10:1, and wherein said washing base is present in the composition in an amount ranging from 4 to 50% by weight relative to the total weight of the composition;

(B) a conditioner system comprising at least one aminated silicone having an amine number ranging from 0.5 meq/g to 5.0 meq/g, said at least one aminated silicone being chosen from:

(a) aminated silicone polymers corresponding to the formula:

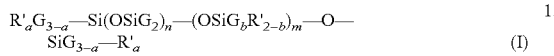

(I)

in which:

G is chosen from OH, and methyl;

a is chosen from 0, 1, 2, and 3;

b is 1;

m and n are chosen from numbers such that the sum (n+m) varies from 1 to 2000;

R' is chosen from monovalent radicals of formula $-C_qH_{2q}L$, wherein q is chosen from a number ranging from 2 to 8 and L is chosen from optionally quaternized amino groups chosen from:

—N(R")—CH$_2$—CH$_2$—N(R")$_2$,

—N(R")$_2$,

—N$^⊕$(R")$_3$A$^-$,

—N$^⊕$H(R")$_2$A$^-$,

—N$^⊕$H$_2$(R")A$^-$, and

—N(R")—CH$_2$—CH$_2$—N$^⊕$R"H$_2$A$^-$, wherein R", which are identical or different, are chosen from a hydrogen atom, and phenyl, benzyl and saturated monovalent hydrocarbon-comprising radicals, and A$^-$ is chosen from organic and inorganic anions; and (b) cationic silicone polymers corresponding to the following formula (IV):

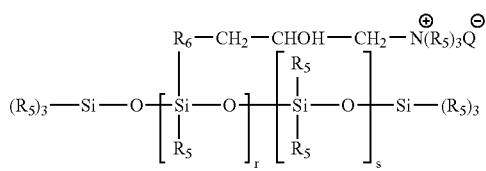

(IV)

in which:

$R_5$ is chosen from monovalent hydrocarbon-comprising radicals having from 1 to 18 carbon atoms;

$R_6$ is chosen from divalent hydrocarbon-comprising radicals;

Q$^-$ is chosen from organic and inorganic anions;

r represents a mean statistical value ranging from 2 to 20;

s represents a mean statistical value ranging from 20 to 200; and (C) at least one cationic polymer;

wherein the composition is transparent.

* * * * *

UNITED STATES PATENT AND TRADEMARK OFFICE
CERTIFICATE OF CORRECTION

PATENT NO. : 7,514,091 B2
APPLICATION NO. : 09/360521
DATED : April 7, 2009
INVENTOR(S) : Serge Restle et al.

It is certified that error appears in the above-identified patent and that said Letters Patent is hereby corrected as shown below:

In claim 1, column 10, line 64, "-N$^P$(R")$_3$A$^-$," should read -- -N $\oplus$ (R")$_3$A$^-$--.

In claim 1, column 10, line 65, "-N$^P$H(R")$_2$A$^-$," should read -- -N $\oplus$ H(R")$_2$A$^-$,--.

In claim 1, column 10, line 66, "-N$^P$H$_2$(R")A$^-$, and" should read -- -N $\oplus$ H$_2$(R")A$^-$, and--.

In claim 1, column 10, line 67, "-N(R")-CH$_2$-CH$_2$-N$^P$R"H$_2$A$^-$," should read
-- -N(R")-CH$_2$-CH$_2$-N $\oplus$ R"H$_2$A$^-$,--.

In claim 1, column 11, lines 9-15,

"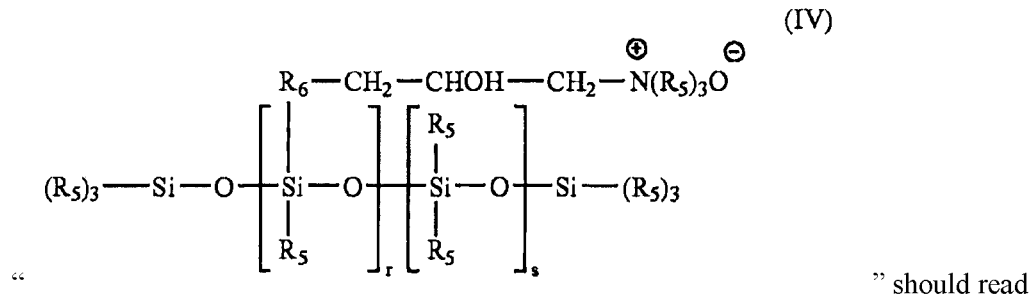" should read

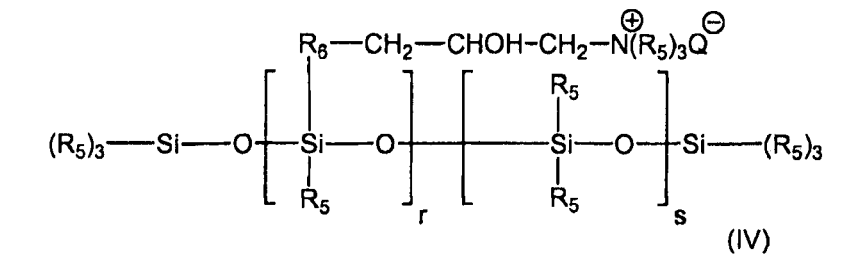
--.

In claim 8, column 11, lines 50-51, "composition an" should read --composition in an--.

Signed and Sealed this

Fourth Day of May, 2010

David J. Kappos
*Director of the United States Patent and Trademark Office*

CERTIFICATE OF CORRECTION (continued)
U.S. Pat. No. 7,514,091 B2

In claim 44, column 14, line 44, "-N$^p$(R")$_3$A$^-$," should read -- -N $\oplus$ (R")$_3$A$^-$,--.

In claim 44, column 14, line 45, "-N$^p$(R")$_2$A$^-$," should read -- -N $\oplus$ H(R")$_2$A$^-$,--.

In claim 44, column 14, line 46, "-N$^p$H$_2$(R")A$^-$, and" should read -- -N $\oplus$ H$_2$(R")A$^-$, and--.

In claim 44, column 14, line 47, "-N(R")-CH$_2$-CH$_2$-N$^p$R"H$_2$A$^-$," should read
-- -N(R")-CH$_2$-CH$_2$-N $\oplus$ R"H$_2$A$^-$,--.

In claim 44, column 14, lines 57-63,

"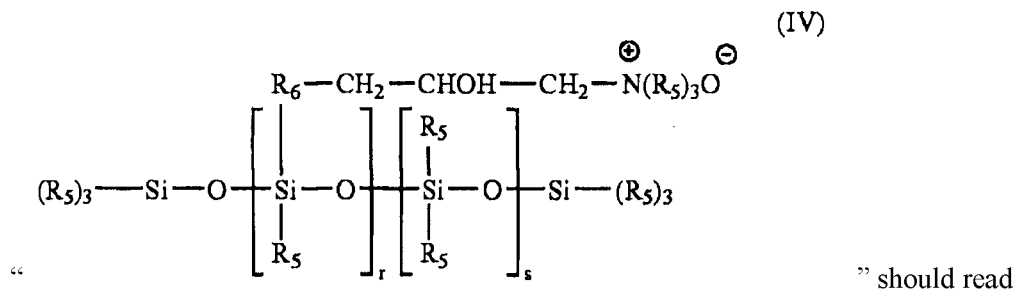" should read

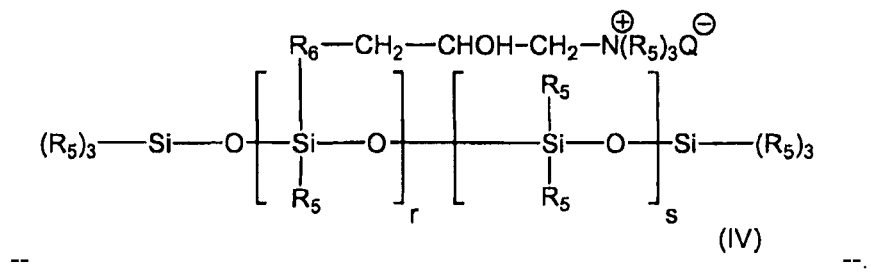

-- --.

In claim 45, column 15, line 36, "-N$^p$(R")$_3$A$^-$," should read -- -N $\oplus$ (R")$_3$A$^-$,--.

In claim 45, column 15, line 37, "-N$^p$H(R")$_2$A$^-$," should read -- -N $\oplus$ H(R")$_2$A$^-$,--.

In claim 45, column 15, line 38, "-N$^p$H$_2$(R")A$^-$, and" should read -- -N $\oplus$ H$_2$(R")A$^-$, and--.

In claim 45, column 15, line 39, "-N(R")-CH$_2$-CH$_2$-N$^p$R"H$_2$A$^-$," should read
-- -N(R")-CH$_2$-CH$_2$-N $\oplus$ R"H$_2$A$^-$,--.

In claim 45, column 15, lines 48-54,

"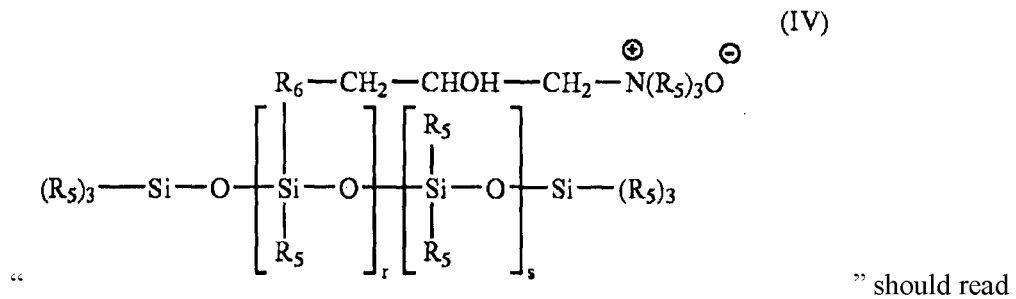" should read

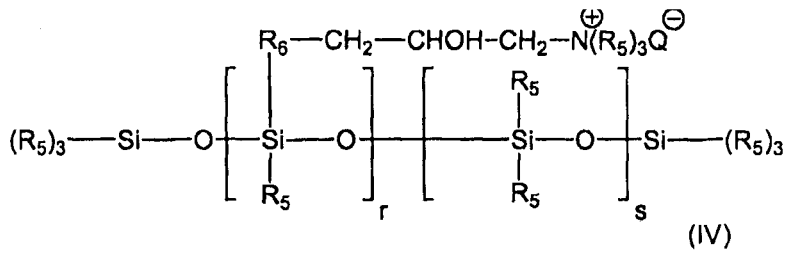

(IV)

In claim 46, column 16, line 35, "-N$^p$(R")$_3$A$^-$," should read -- -N $\oplus$ (R")$_3$A$^-$,--.

In claim 46, column 16, line 36, "-N$^p$H(R")$_2$A$^-$," should read -- -N $\oplus$ H(R")$_2$A$^-$,--.

In claim 46, column 16, line 37, "-N$^p$H$_2$(R")A$^-$, and" should read -- -N $\oplus$ H$_2$(R")A$^-$, and--.

In claim 46, column 16, line 38, "-N(R")-CH$_2$-CH$_2$-N$^p$R"H$_2$A$^-$," should read -- -N(R")-CH$_2$-CH$_2$-N $\oplus$ R"H$_2$A$^-$,--.

In claim 47, column 17, line 30, "-N$^p$(R")$_3$A$^-$," should read -- -N $\oplus$ (R")$_3$A$^-$,--.

In claim 47, column 17, line 31, "-N$^p$H(R")$_2$A$^-$," should read -- -N $\oplus$ H(R")$_2$A$^-$,--.

In claim 47, column 18, line 1, "-N$^p$H$_2$(R")A$^-$, and" should read -- -N $\oplus$ H$_2$(R")A$^-$, and--.

In claim 47, column 18, line 2, "-N(R")-CH$_2$-CH$_2$-N$^p$R"H$_2$A$^-$," should read -- -N(R")-CH$_2$-CH$_2$-N $\oplus$ R"H$_2$A$^-$,--.